United States Patent
Takasawa

(10) Patent No.: US 10,470,736 B2
(45) Date of Patent: Nov. 12, 2019

(54) RADIOGRAPHING SYSTEM AND METHOD FOR CONTROLLING RADIOGRAPHING APPARATUSES

(71) Applicant: CANON KABUSHIKI KAISHA, Tokyo (JP)

(72) Inventor: Toru Takasawa, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 384 days.

(21) Appl. No.: 15/494,278

(22) Filed: Apr. 21, 2017

(65) Prior Publication Data
US 2017/0303884 A1    Oct. 26, 2017

(30) Foreign Application Priority Data

Apr. 25, 2016  (JP) ................. 2016-087441

(51) Int. Cl.
*A61B 6/00* (2006.01)
*A61B 6/10* (2006.01)
(52) U.S. Cl.
CPC ............ *A61B 6/54* (2013.01); *A61B 6/467* (2013.01); *A61B 6/548* (2013.01); *A61B 6/465* (2013.01)

(58) Field of Classification Search
CPC ........... A61B 6/465; A61B 6/467; A61B 6/54; A61B 6/548
See application file for complete search history.

(56) References Cited

U.S. PATENT DOCUMENTS

| | | | | |
|---|---|---|---|---|
| 2012/0207278 A1* | 8/2012 | Yonekawa | ........... | A61B 6/4233 378/98.5 |
| 2015/0279196 A1* | 10/2015 | Tajima | ................. | G08B 13/22 340/539.32 |

FOREIGN PATENT DOCUMENTS

JP    20156413 A    1/2015

\* cited by examiner

*Primary Examiner* — Mark R Gaworecki
(74) *Attorney, Agent, or Firm* — Canon U.S.A., Inc. IP Division

(57) ABSTRACT

A radiographing system including a plurality of radiographing apparatuses for detecting a radiation and a control apparatus for controlling a plurality of the radiographing apparatuses includes an enabling instruct unit for issuing an instruction for enabling one radiographing apparatus from a plurality of the radiographing apparatuses. When the instruction for enabling one radiographing apparatus is issued from the enabling instruct unit, the control apparatus restricts the enabling of another radiographing apparatus during a predetermined period of time after receiving the enabling instruction.

15 Claims, 13 Drawing Sheets

FIG. 6

| INDEX | NAME | SERIAL No. | STATUS |
|---|---|---|---|
| #01 | RADIOGRAPHING APPARATUS A | A00001 | DISABLED |
| #02 | RADIOGRAPHING APPARATUS B | B00001 | ENABLED |
|  |  |  |  |

230

RADIOGRAPHING SYSTEM AND METHOD FOR CONTROLLING RADIOGRAPHING APPARATUSES

BACKGROUND OF THE INVENTION

Field of the Invention

The present invention relates to a radiographing system using radiographing apparatuses for imaging a subject by using a radiation, and a method for controlling the radiographing apparatuses.

Description of the Related Art

A conventional radiographing system includes a radiation generating apparatus for irradiating the subject with a radiation, and a radiographing apparatus for generating a radiographic image as an intensity distribution of a radiation through the subject.

In recent years, a radiographing apparatus capable of taking a radiographic image by automatically detecting a radiation without synchronizing irradiation timing with a radiation generating apparatus has been developed. This radiographing apparatus does not need a cable for synchronization with the radiation generating apparatus.

Radiographing apparatuses handle various image sizes including 14×14 inch (356×356 mm), 17×17 inch (432×432 mm), and 11×14 inch (279×356 mm). Radiographing apparatuses are installed on a stand or bed to perform imaging based on various imaging techniques. For example, a 11×14 inch radiographing apparatus is used for imaging fingers, and a 17×17 inch radiographing apparatus is used for abdominal imaging. If the subject's lower half of the body is not robust and the subject is unable to endure the imaging in a standing position, the radiographing apparatus to be used is changed from stand type to bed type taking subject's conditions into consideration at the time of imaging. This radiographing apparatus switching is performed via an operation unit connected to a control apparatus.

Imaging is performed by switching a plurality of radiographing apparatuses in this way. Generally, a console for controlling radiation and an operation unit for operating radiographing apparatuses are installed in another operation room which is different from an imaging room in which imaging is performed.

An operator selects a radiographing apparatus suitable for the target imaging technique by using the operation unit in the operation room, returns to the imaging room, and positions the subject according to the selected radiographing apparatus. For example, when selecting a different radiographing apparatus because a size of the current radiographing apparatus is not suitable for the imaging, the operator conventionally had to return to the operation room and perform a related operation.

Therefore, using a selection button provided on the radiographing apparatuses, the operator selects the radiographing apparatus to be used for imaging by associating the selected radiographing apparatus with examinee information. For example, Japanese Patent Application Laid-Open No. 2015-6413 does not describe control for enabling or disabling a plurality of radiographing apparatuses. Further, for example, the operator may possibly perform the imaging by using a radiographing apparatus which is not ready for the imaging, i.e., the apparatus in the disabled state, by mistake.

SUMMARY OF THE INVENTION

According to an aspect of the present invention, a radiographing system suitably performs control to enable or disable a plurality of radiographing apparatuses. According to another aspect of the present invention, a method for controlling the radiographing apparatuses is provided.

According to another aspect of the present invention, each of the radiographing apparatuses includes an enabling instruct unit for enabling each radiographing apparatus. When an instruction for enabling one radiographing apparatus is issued from the enabling instruct unit, a control apparatus restricts the enabling of another radiographing apparatus during a predetermined period of time after receiving the enabling instruction. Further, when the enabling instruct unit enables one radiographing apparatus, the control apparatus performs processing for disabling another radiographing apparatus.

Further features of the present invention will become apparent from the following description of example embodiments with reference to the attached drawings.

BRIEF DESCRIPTION OF THE DRAWINGS

FIG. 6 illustrates a table based on a status of the radiographing apparatus according to the present invention.

DESCRIPTION OF THE EMBODIMENTS

Favorable example embodiments of the present invention will be described below with reference to the accompanying drawings.

A radiographing system and a method for controlling a plurality of radiographing apparatuses according to a first example embodiment will be described below with reference to the accompanying drawings.

Figure 1:
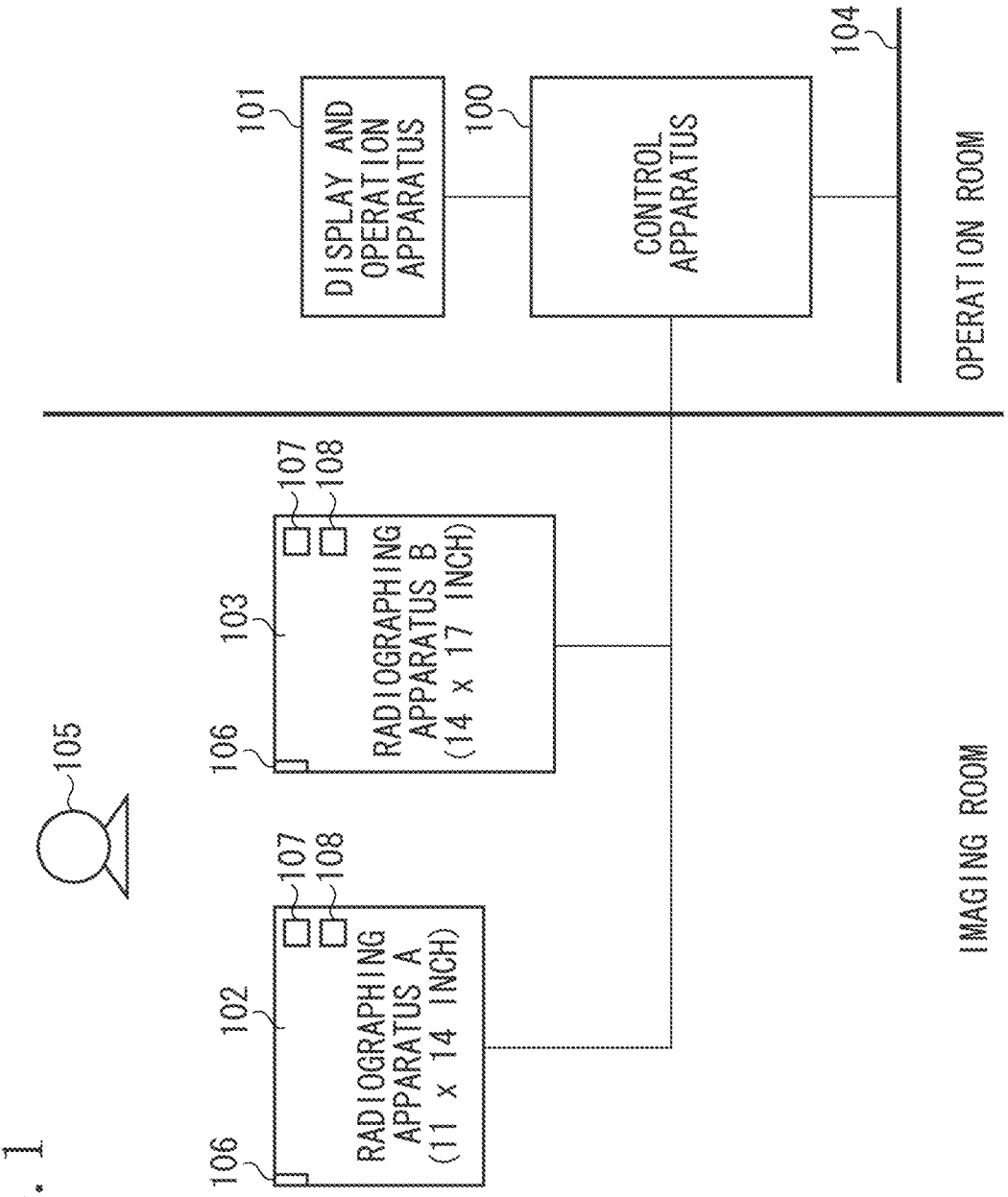
FIG. 1 is a block diagram schematically illustrating a configuration of a radiographing system according to the present invention.

FIG. 1 schematically illustrates a configuration of the radiographing system according to the first example embodiment. The radiographing system includes a radiation generating apparatus 105 for generating a radiation, and radiographing apparatuses 102 and 103 for detecting a radiation through a subject to generate a radiographic image. The radiographing system further includes a display and operation apparatus 101 for displaying a radiographic image and performing an operation, and a control apparatus 100 for controlling each component.

The radiation generating apparatus 105 and the radiographing apparatuses 102 and 103 are installed in an imaging room, and the display and operation apparatus 101 and the control apparatus 100 are installed in an operation room.

The radiation generating apparatus 105 generates a radiation, and includes an X-ray tube for emitting a radiation, and a diaphragm for limiting the irradiation region of a radiation. After setting imaging conditions including the tube voltage and tube current to the radiation generating apparatus 105, an operator can emit a radiation from the radiation generating apparatus 105 by pressing an irradiation switch (not illustrated).

The radiographing apparatuses 102 and 103 (flat panel detectors (FPD)) include a scintillator for emitting light according to the radiation energy, and a photoelectric converter for converting light into an electrical signal. The radiographing apparatuses 102 and 103 may directly convert a radiation into an electrical signal. The radiographing apparatuses 102 and 103 are communicably connected to the control apparatus 100 via a wired or wireless communication method (not illustrated). The radiographing apparatuses 102 and 103 are installed on a top side or in the inside of an examination bed depending on an imaging target portion of the subject.

The radiographing apparatus 102 is a radiographing apparatus A, and the radiographing apparatus 103 is a radiographing apparatus B. The radiographing apparatuses A and B detect a radiation through the subject, and output the radiation distribution as a radiographic image. Although the radiographing apparatuses A and B are different in size, the radiographing apparatuses A and B have the same function. The radiographing apparatus A is used for the 11×14 inch (279×356 mm) image size while the radiographing apparatus B is used for the 14×17 inch (356×432 mm) image size. The radiographing apparatus A is used for small imaging regions such as fingers and limbs. The radiographing apparatus B is used for wide imaging regions such as the chest and abdomen.

The control apparatus 100 controls the radiographing apparatus A, the radiographing apparatus B, and the display and operation apparatus 101. The control apparatus 100 performs data communication of examinee information, inspection information, and radiographic images via an in-hospital network 104. In response to an operator's instruction, the control apparatus 100 instructs the radiographing apparatuses A and B to enter an enabled state or a disabled state. When the control apparatus 100 enables the radiographing apparatus A to enter the enabled state, the operator can perform imaging by using the radiographing apparatus A. Likewise, when the control apparatus 100 enables the radiographing apparatus B to make the enabled state, the operator can perform the imaging by using the radiographing apparatus B.

The control apparatus 100 performs correction processing (such as offset correction and gain correction) and image processing (such as gradation conversion) on radiographic images transmitted from the radiographing apparatuses A and B to generates images. The display and operation apparatus 101 displays an image output from the control apparatus 100.

The enabled state refers to a state where the reading circuit of a radiographing apparatus is operating and able to acquire radiographic image data in response to the emission of a radiation. A radiographing apparatus of automatic detection type for automatically detecting a radiation can detect a radiation in the enabled state. The enabled state is what is referred to as a Ready state. The Ready state refers to a state where a cycle of a radiation store operation and a radiation read operation is repetitively performed. When a radiation is not emitted, the radiographing apparatus performs the read operation (dummy read) and applies a dark current. In the Ready state, the level of the dark current of the radiographing apparatus can be stabilized by repetitively performing the store and read operations.

On the other hand, the disabled state refers to a state where radiographic image data cannot be acquired even if a radiation is emitted because power is not supplied to the reading circuit or an electric current level is low. The disabled state is what is referred to as a Sleep state. The Sleep state is a state where imaging preparation is not completed because of a low voltage applied for a radiation. In the Sleep state, the bias lines are set to the ground level to set the potential of all common electrodes to the ground level. The radiographing apparatus of automatic detection type for automatically detecting a radiation cannot detect a radiation in the disabled state.

The radiographing apparatuses A and B can operate in either one of the disabled state (Sleep state) where the power consumption is lowered and a radiographic image cannot be generated and the enabled state (Ready state) where a radiographic image can be generated.

The radiographing apparatus A includes a status display unit 106 for indicating the enabled state (Ready state) where a radiographic image can be generated, and an enabling instruct unit 107 for enabling the radiographing apparatus A to enter the enabled state (Ready state) where a radiographic image can be generated. The radiographing apparatus B includes a status display unit 106 for indicating the enabled state (Ready state) where a radiographic image can be generated, and an enabling instruct unit 107 for enabling the radiographing apparatus B to enter the enabled state (Ready state) where a radiographic image can be generated. The enabling instruct unit 107 may be included in either one of the radiographing apparatuses A and B, and be configured to issue an enabling instruction for enabling a plurality of radiographing apparatuses. The display and operation apparatus 101 may include the enabling instruct unit 107 for enabling the radiographing apparatuses A and B.

The radiographing apparatus A includes a disabling instruct unit 108 for disabling the radiographing apparatus A to enter the disabled state (Sleep state) where a radiographic image cannot be generated. The radiographing apparatus B includes the disabling instruct unit 108 for disabling the radiographing apparatus B to enter the disabled state (Sleep state) where a radiographic image cannot be generated.

The status display unit 106 provided in the radiographing apparatuses A and B is, for example, a lamp which lights up in green. The enabling instruct unit 107 and the disabling instruct unit 108 are respectively provided as a button. Although the enabling instruct unit 107 and the disabling instruct unit 108 are provided in each of the radiographing apparatuses A and B, each radiographing apparatus may be enabled or disabled by turning one button ON or OFF.

Further, only the enabling instruct unit 107 may be provided in each of the radiographing apparatuses A and B.

As illustrated in FIG. 1, the radiographing apparatuses A and B include the status display unit 106, the enabling instruct unit 107, and the disabling instruct unit 108 provided at the same positions.

When the operator presses the enabling instruct unit 107 of the radiographing apparatus A, the radiographing apparatus A is enabled and enters the enabled state where the status display unit 106 lights up in green. When the operator presses the disabling instruct unit 108 of the radiographing apparatus A, the radiographing apparatus A is disabled and enters the disabled state where the status display unit 106 turns OFF. The operator can figure out whether the radiographing apparatus A is in the enabled or disabled state according to the lighting state of the status display unit 106.

Likewise, when the operator presses the enabling instruct unit 107 of the radiographing apparatus B, the radiographing apparatus B is enabled and enters the enabled state where the status display unit 106 lights up in green. When the operator presses the disabling instruct unit 108 of the radiographing apparatus B, the radiographing apparatus B is disabled and enters the disabled state where the status display unit 106 turns OFF. The operator can figure out whether the radiographing apparatus A or B is in the enabled state or in the disabled state according to the lighting state of the status display unit 106.

The display and operation apparatus 101 displays radiographic images taken by the radiographing apparatuses A and B. The display and operation apparatus 101 operates the radiographing system and the radiographing apparatuses A and B. Although the display and operation apparatus 101 is generally used with a touch-panel monitor, it may also be combined with input devices such as a mouse, a keyboard, a magnetic card, and a bar code.

Figure 2:
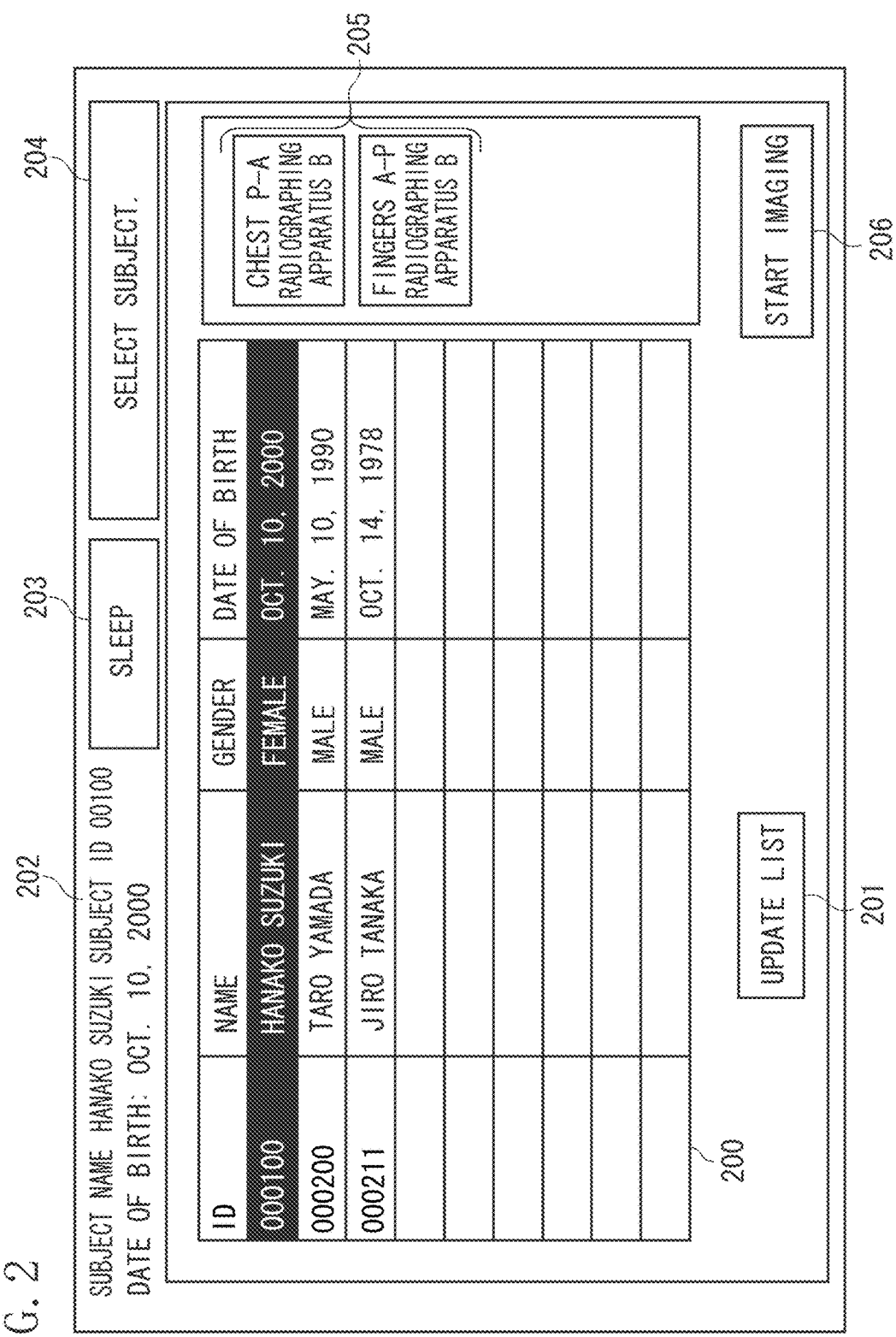
FIG. 2 illustrates an example of an imaging preparation screen of the radiographing system according to the present invention.
Figure 3:
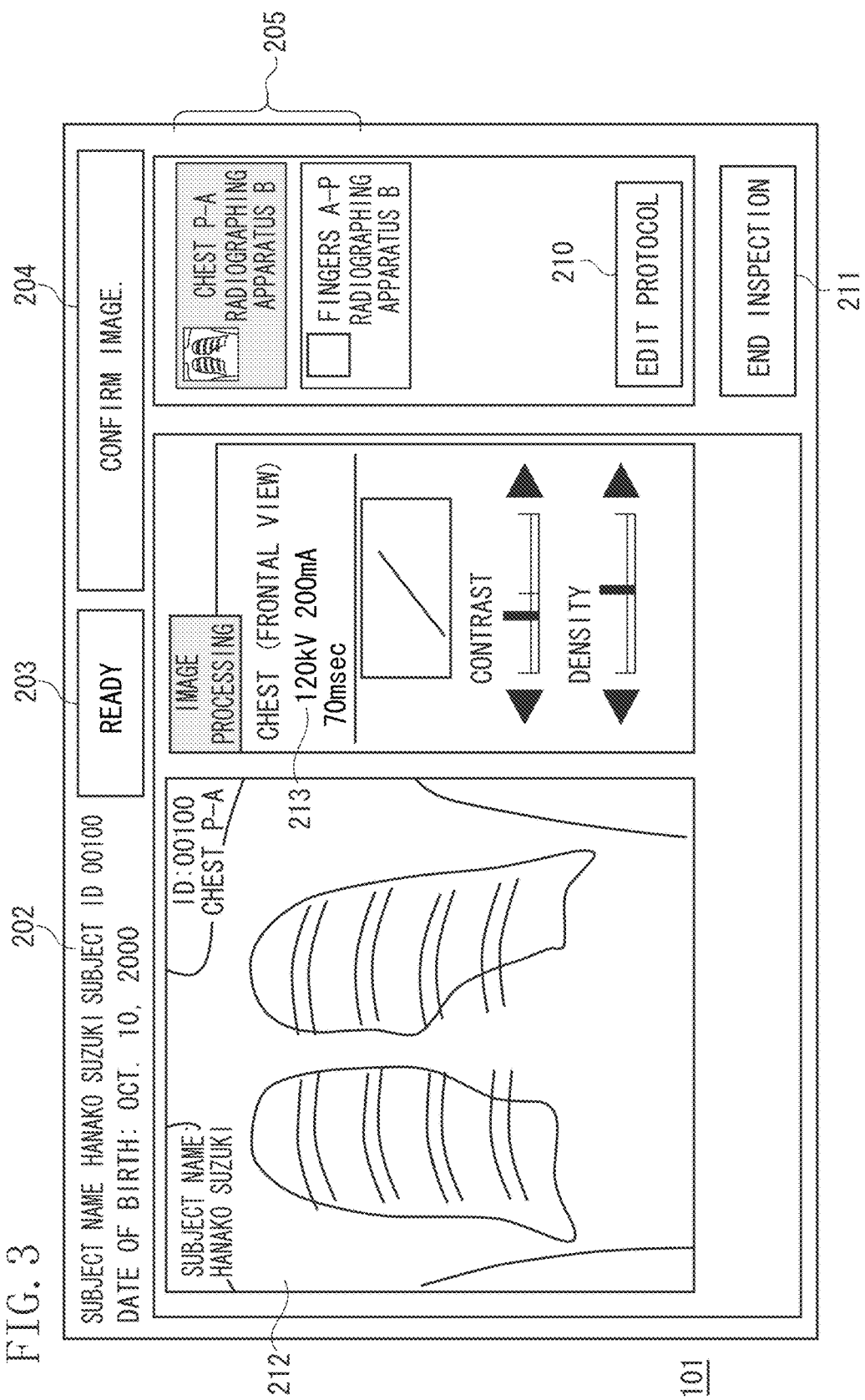
FIG. 3 illustrates an example of an imaging screen of the radiographing system according to the present invention.

FIGS. 2 and 3 illustrate examples of graphical user interface (GUI) screens displayed on the display and operation apparatus 101. FIG. 2 illustrates an imaging preparation screen, and FIG. 3 illustrates an image screen after taking an image.

FIG. 2 illustrates a state where examinee information and inspection information transmitted from a radiology information system (RIS) via the in-hospital network 104 are displayed in the display and operation apparatus 101 as an imaging order list 200. The operator selects a subject from the imaging order list 200, confirms the subject in an examinee information display area 202 and a protocol display area 205, and presses a Start Imaging button 206. The protocol display area 205 displays protocols in order of imaging processing, which will be sequentially executed from the top downward. A protocol includes a combination of an imaging target portion, an imaging direction, and a radiographing apparatus to be used. When the operator specifies a protocol, the control apparatus 100 determines the imaging target portion, the imaging direction, and the radiographing apparatus to be used. Then, the control apparatus 100 determines image processing to be used for radiographic images and calibration data for each radiographing apparatus.

An Update List button 201 is used to update the imaging order list 200. By pressing the Update List button 201, the imaging order list 200 transmitted from RIS can be updated.

Figure 4:
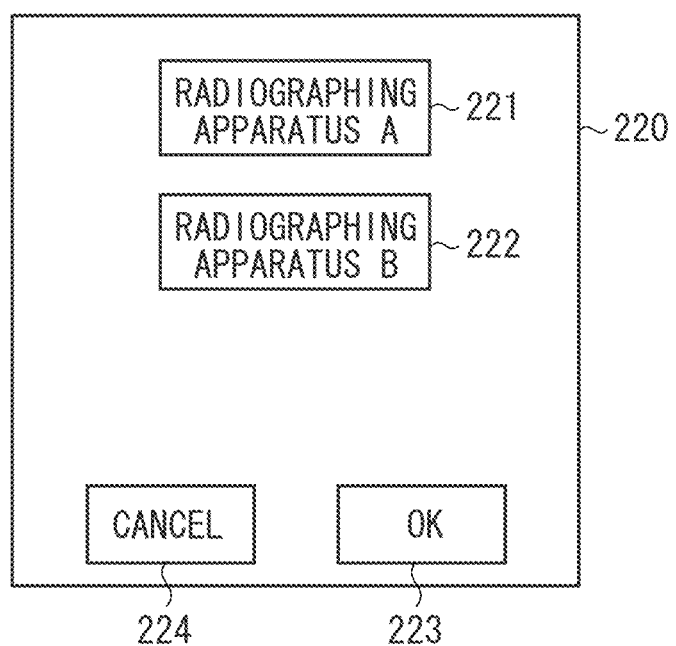
FIG. 4 illustrates an example of a radiographing apparatus selection window according to the present invention.

FIG. 3 illustrates a state where a radiographic image is displayed on the display and operation apparatus 101. A taken radiographic image is displayed in an image display area 212. By adjusting each image processing in a tool box 213, the contrast, density, and sharpness of image can be adjusted. In the protocol display area 205, an upper stage indicates that imaging of a chest P-A is completed and that a radiographic image is displayed in the image display area 212. A lower stage currently being focused indicates that fingers A-P will be subsequently imaged. An Edit Protocol button 210 allows the operator to change the radiographing apparatus of the currently focused protocol. When the operator presses the Edit Protocol button 210, a radiographing apparatus selection window illustrated in FIG. 4 is called which allows the operator to select a radiographing apparatus. In the present case, the operator can press a selection button 221 for the radiographing apparatus A or a selection button 222 for the radiographing apparatus B. By pressing an OK button 223, the selection of the selection button 221 or 222 is chosen. By pressing a Cancel button 224, the selection of the selection button 221 or 222 is cancelled. The control apparatus 100 enables the radiographing apparatus chosen by the selection button 221 or 222 to enter the enabled state (Ready state) where a radiographic image can be generated. More specifically, the operator can select the radiographing apparatus A or B to be used for imaging via the display and operation apparatus 101. The operator can enable or disable the radiographing apparatuses A and B to be used for imaging via the display and operation apparatus 101.

Figure 5:
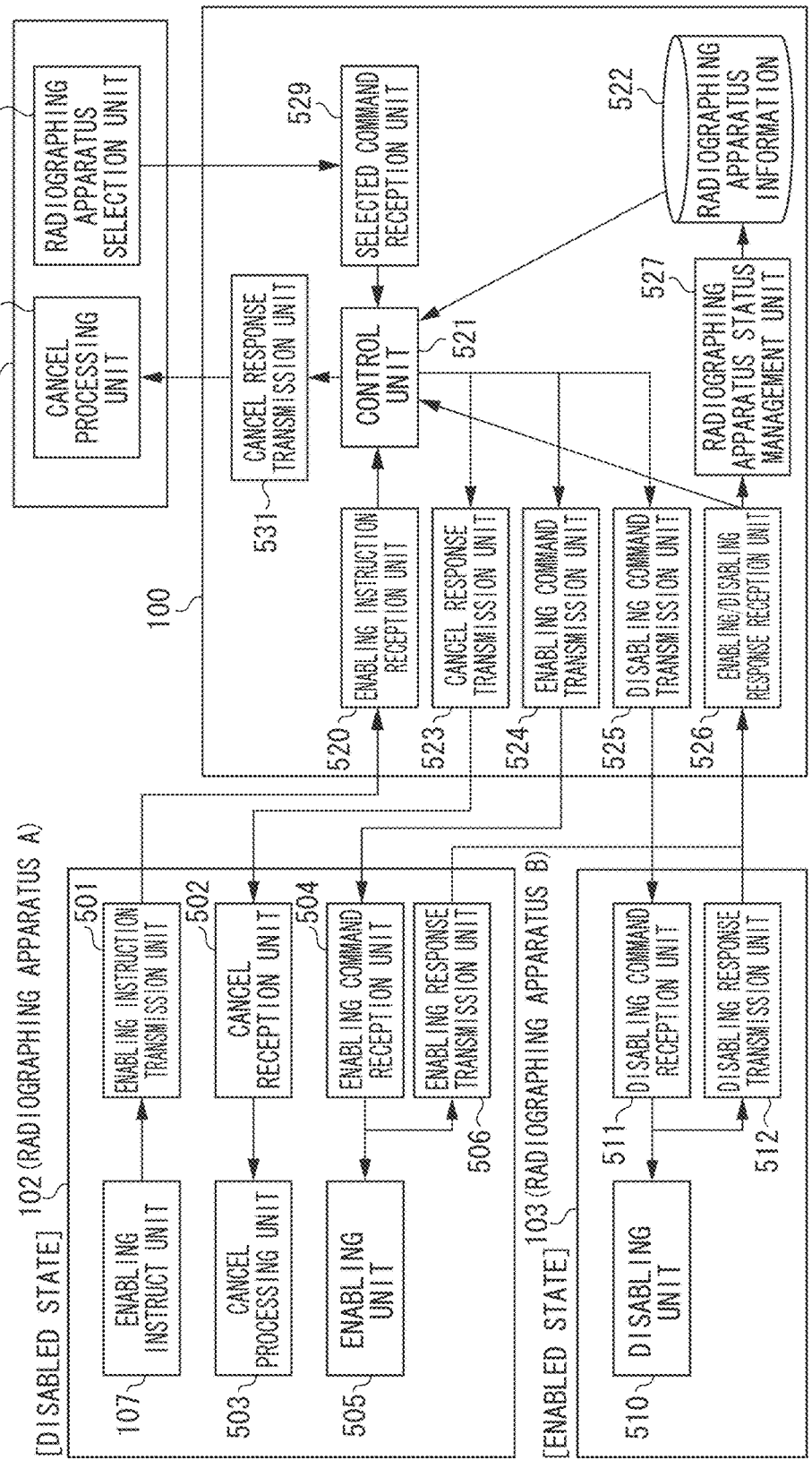
FIG. 5 is a block diagram illustrating a configuration according to a first example embodiment of the present invention.

FIG. 5 is a block diagram illustrating a configuration of the first example embodiment of the present invention. FIG. 5 illustrates the states of the radiographing apparatuses A and B. To simplify the illustration, the radiographing apparatus A (radiographing apparatus 102) is in the disabled state (Sleep state), and the radiographing apparatus B (radiographing apparatus 103) is in the enabled state (Ready state).

The radiographing apparatus A includes the enabling instruct unit 107 for issuing an instruction for enabling the radiographing apparatus A currently kept in the disabled state, and an enabling instruction transmission unit 501 for transmitting a signal for enabling the radiographing apparatus A to the control apparatus 100.

The radiographing apparatus A includes a cancel reception unit 502 for receiving a cancel response from the control apparatus 100 when the control apparatus 100 cancels an enabling instruction from the enabling instruction transmission unit 501. The radiographing apparatus A includes a cancel processing unit 503 for cancelling the enabling of the radiographing apparatus A based on a cancel response from the control apparatus 100.

The radiographing apparatus A further includes an enabling command reception unit 504 for receiving an enabling command from the control apparatus 100 when the control apparatus 100 accepts (permits) an enabling instruction from the enabling instruction transmission unit 501. The radiographing apparatus A further includes an enabling unit 505 and an enabling response transmission unit 506. The enabling unit 505 enables the radiographing apparatus A to enter the enabled state. The enabling response transmission unit 506 transmits an enabling response signal indicating that the radiographing apparatus A has been enabled, to the control apparatus 100. The enabling response signal transmitted from the radiographing apparatus A allows the control apparatus 100 to recognize that the radiographing apparatus A has entered the enabled state.

The radiographing apparatus B includes a disabling command reception unit 511 for receiving a disabling command from the control apparatus 100 when the control apparatus 100 accepts an enabling instruction from the enabling instruction transmission unit 501. The radiographing apparatus B further includes a disabling unit 510 for disabling the radiographing apparatus B to enter the disabled state, and a disabling response transmission unit 512 for transmitting a disabling response signal indicating that the radiographing apparatus B has been disabled, to the control apparatus 100. The disabling response signal transmitted from the radiographing apparatus B allows the control apparatus 100 to recognize that the radiographing apparatus B has entered the disabled state.

In the above-described form, the radiographing apparatus A is in the disabled state and the radiographing apparatus B is the enabled state. However, the radiographing apparatus B may be in the disabled state and the radiographing apparatus A may be in the enabled state. Although the form illustrated in FIG. 5 is used to simplify the illustration, each of the radiographing apparatuses A and B includes the enabling instruct unit 107, the enabling instruction transmission unit 501, the cancel reception unit 502, the cancel processing unit 503, the enabling command reception unit 504, the enabling unit 505, the enabling response transmission unit 506, the disabling unit 510, the disabling command reception unit 511, and the disabling response transmission unit 512.

The control apparatus 100 includes an enabling instruction reception unit 520 for receiving a signal related to an enabling instruction for enabling the radiographing apparatus A. The control apparatus 100 further includes a cancel response transmission unit 523 for transmitting a cancel response to the radiographing apparatus A when the control apparatus 100 cancels an enabling instruction received from the enabling instruction transmission unit 501, and an enabling command transmission unit 524 for transmitting a disabling command to the radiographing apparatus A. The control apparatus 100 further includes a disabling command transmission unit 525 for transmitting a disabling command to the radiographing apparatus B. The control apparatus 100 further includes an enabling/disabling response reception unit 526 for receiving from the disabling response transmission unit 512 an enabling response indicating that the radiographing apparatus A has been enabled so as to enter the enabled state from the enabling response transmission unit 506 and a disabling response indicating that the radiographing apparatus B has been disabled so as to enter the disabled state. The control apparatus 100 further includes a radiographing apparatus status management unit 527 for managing the statuses of the radiographing apparatuses A and B. The control apparatus 100 further includes a radiographing apparatus information storage unit 522 for storing information about the radiographing apparatuses A and B.

The display and operation apparatus 101 includes a radiographing apparatus selection unit 540 for selecting a radiographing apparatus to be used for imaging, and a cancel processing unit 541 for canceling the enabling based on a cancel response from the control apparatus 100. The radiographing apparatus selection unit 540 is connected to the control apparatus 100 and used to select one radiographing apparatus from a plurality of radiographing apparatuses for detecting a radiation. More specifically, in the radiographing system according to the present example embodiment, a radiographing apparatus to be used for imaging can be selected from the enabling instruct units 107 of the radiographing apparatuses 102 and 103, and the display and operation apparatus 101.

The control apparatus 100 further includes a selected command reception unit 529 for receiving selection information from the radiographing apparatus selection unit 540, and a cancel response transmission unit 531 for transmitting a cancel response to the display and operation apparatus 101 when the control apparatus 100 cancels select the instruction received from the radiographing apparatus selection unit 540. A control unit 521 controls the above-described components in the control apparatus 100.

An imaging technique according to the present invention will be described below. When the operator selects a subject and then presses the Start Imaging button 206 in the imaging preparation screen illustrated in FIG. 2, the chest P-A protocol as the first protocol is automatically pressed. The screen shifts to the imaging screen, and the radiographing apparatus B is enabled and a status display unit 106 of the radiographing apparatus B turns ON. In the imaging room, the operator positions the subject to set a suitable relative position between the radiographing apparatus B and the subject. Then, the operator goes to the operation room from the imaging room, and checks whether the imaging conditions are correct at the console of the radiation generating apparatus 105. When the imaging conditions are correct, the operator presses the irradiation switch to emit a radiation.

The radiation through the subject is detected by the radiographing apparatus B, and then transmitted to the control apparatus 100 as image data. The control apparatus 100 performs correction processing by using calibration data corresponding to the radiographing apparatus B, and then performs various image processing such as contrast adjustment, density adjustment, sharpness adjustment, and dynamic compression to generate a radiographic image. The generated radiographic image is transmitted to the display and operation apparatus 101, and then displayed in the image display area 212 of the imaging screen illustrated in FIG. 3.

At the same time, the fingers A-P is focused as the next imaging protocol, and the radiographing apparatus B becomes ready for the following imaging. Then, the operator returns to the imaging room and performs positioning to image the subject's fingers by using the radiographing apparatus B kept in the enabled state. Since the subject's fingers have a narrow imaging region, the 43×43 cm size is not necessary. Accordingly, the operator selects the radiographing apparatus A for a one-rank smaller size (11×14 inch) in the imaging room. The operator presses the enabling instruct unit 107 provided as a button on the radiographing apparatus A. Instead of a button, the enabling instruct unit 107 illustrated in FIG. 5 may be a switch or a speech input device as long as an enabling instruction can be issued.

When the operator inputs a request for enabling the radiographing apparatus A into the enabling instruct unit 107, a signal related to the instruction for enabling the radiographing apparatus A is transmitted to the control apparatus 100. The transmitted signal is received by the enabling instruction reception unit 520. The control unit 521 determines whether the radiographing apparatus A can be enabled. When the other radiographing apparatus B is not currently being controlled (used), the control unit 521 permits the enabling of the radiographing apparatus A. On the other hand, when another radiographing apparatus B is currently being controlled (used), the control unit 521 disables another radiographing apparatus B and then enables the radiographing apparatus A which has received the enabling instruction.

If the control unit 521 does not permit the enabling of the radiographing apparatus A, a cancel response is transmitted from the cancel response transmission unit 523 to the radiographing apparatus A. The cancel response transmitted by the cancel response transmission unit 523 is received by the cancel reception unit 502. The cancel processing unit 503 cancels the enabling of the radiographing apparatus A. More specifically, the radiographing apparatus A enters the disabled state. The cancel processing unit 503 instructs the radiographing apparatus A to display cancel information indicating that the enabling of the radiographing apparatus A has been cancelled. For example, the cancel processing unit 503 generates an electronic sound such as a pip sound from the radiographing apparatus A to feed back to the operator the information indicating that pressing of the enabling instruct unit 107 has not worked. The display and operation apparatus 101 may display cancel information indicating that the enabling of the radiographing apparatus A has been canceled.

When the control unit 521 permits the enabling of the radiographing apparatus A, the control unit 521 performs exclusion processing so that a transition request from another radiographing apparatus B may not interrupt the processing. The control unit 521 performs the exclusion processing, for example, by using a semaphore or mutex. More specifically, when the enabling instruct unit 107 instructs the processing for enabling one radiographing apparatus, the control apparatus 100 restricts the enabling processing for another radiographing apparatus B during a predetermined period of time after the enabling processing is performed.

FIG. 6 illustrates a table indicating the statuses of radiographing apparatuses A and B. Based on a table 230 illustrated in FIG. 6, according to information about the radiographing apparatuses A and B stored in the radiographing apparatus information storage unit 522, the control apparatus 100 can also disable the radiographing apparatus B kept in the enabled state. More specifically, a disabling command is transmitted from the disabling command transmission unit 525. The transmitted disabling command is received by the disabling command reception unit 511 of the radiographing apparatus B. The disabling command is transmitted to the disabling unit 510, and the disabling unit 510 disables the radiographing apparatus B to enter the disabled state. The radiographing apparatus B turns OFF the status display unit 106. More specifically, when the operator performs the processing for enabling one radiographing apparatus A via the enabling instruct unit 107, the control apparatus 100 performs the processing for disabling another radiographing apparatus B.

Upon completion of the disabling of the radiographing apparatus B, a disabling response indicating that the radiographing apparatus B has entered the disabled state is transmitted from the disabling response transmission unit 512 to the control apparatus 100. In the control apparatus 100, the transmitted disabling response is received by the enabling/disabling response reception unit 526. After the control apparatus 100 confirms that the enabling/disabling response reception unit 526 has received the disabling response, an enabling command for enabling the radiographing apparatus A is transmitted from the enabling command transmission unit 524 to the radiographing apparatus A. Then, the radiographing apparatus status management unit 527 updates the information in the radiographing apparatus information storage unit 522. In the radiographing apparatus A, upon reception of the enabling command from the enabling command reception unit 504, the enabling unit 505 enables the radiographing apparatus A to enter the enabled state. When the radiographing apparatus A enters the enabled state, the status display unit 106 turns ON. An enabling response of the radiographing apparatus A is transmitted from the enabling response transmission unit 506 to the control apparatus 100. More specifically, after disabling the other radiographing apparatus B, the control apparatus 100 enables the radiographing apparatus A which has received the enabling instruction. This processing prevents a plurality of radiographing apparatuses from being simultaneously enabled, i.e., from simultaneously entering the Ready state.

In the control apparatus 100, the enabling response is received by the enabling/disabling response reception unit 526, the control unit 521 completes the exclusion processing, and the radiographing apparatus status management unit 527 updates the contents of the information stored in the radiographing apparatus information storage unit 522.

In this configuration, the radiographing apparatus A is enabled and enters the enabled state. Along with it, the radiographing apparatus A becomes ready for imaging the subject's fingers, while the radiographing apparatus B which is not used is disabled and enters the disabled state.

Further, by pressing the Edit Protocol button 210 in the imaging screen illustrated in FIG. 3, the operator can select the radiographing apparatus A or B in a radiographing apparatus selection window 220 illustrated in FIG. 4. In the imaging room, when the operator presses the enabling instruct unit 107 of the radiographing apparatus A and then presses the selection button 221 or 222 during a radiographing apparatus switching process, the operation is cancelled. More specifically, during a predetermined period of time after the processing for enabling the radiographing apparatus A, the control apparatus 100 restricts the enabling of another radiographing apparatus B. The control apparatus 100 gives priority to the processing for enabling the radiographing apparatus A for which the instruction is input first.

When the operator presses the radiographing apparatus A selection button 221 or the radiographing apparatus B selection button 222 which is the radiographing apparatus selection unit 540 of the display and operation apparatus 101, a radiographing apparatus selection command is transmitted from the radiographing apparatus selection unit 540 to the control apparatus 100. The control unit 521 disables another radiographing apparatus B, and then enables the radiographing apparatus A selected on the display and operation apparatus 101. This prevents a plurality of radiographing apparatuses from being simultaneously enabled and from simultaneously entering the Ready state.

Figure 7:
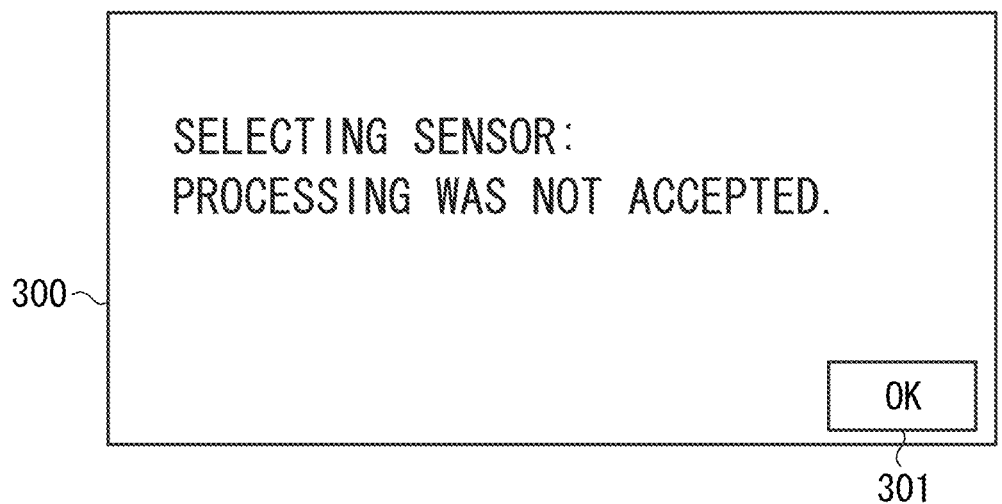
FIG. 7 illustrates an example of a dialog according to the present invention.

The transmitted radiographing apparatus selection command is received by the selected command reception unit 529. Then, the control unit 521 determines whether the exclusion processing for the radiographing apparatus A or B is currently being performed. When the exclusion processing is currently being performed, a cancel response is transmitted from the cancel response transmission unit 531 to the display and operation apparatus 101. The cancel processing unit 541 receives the cancel response and performs the cancel processing. The display and operation apparatus 101 displays an alert dialog as illustrated in FIG. 7, which is an example of cancel processing.

Figure 8:
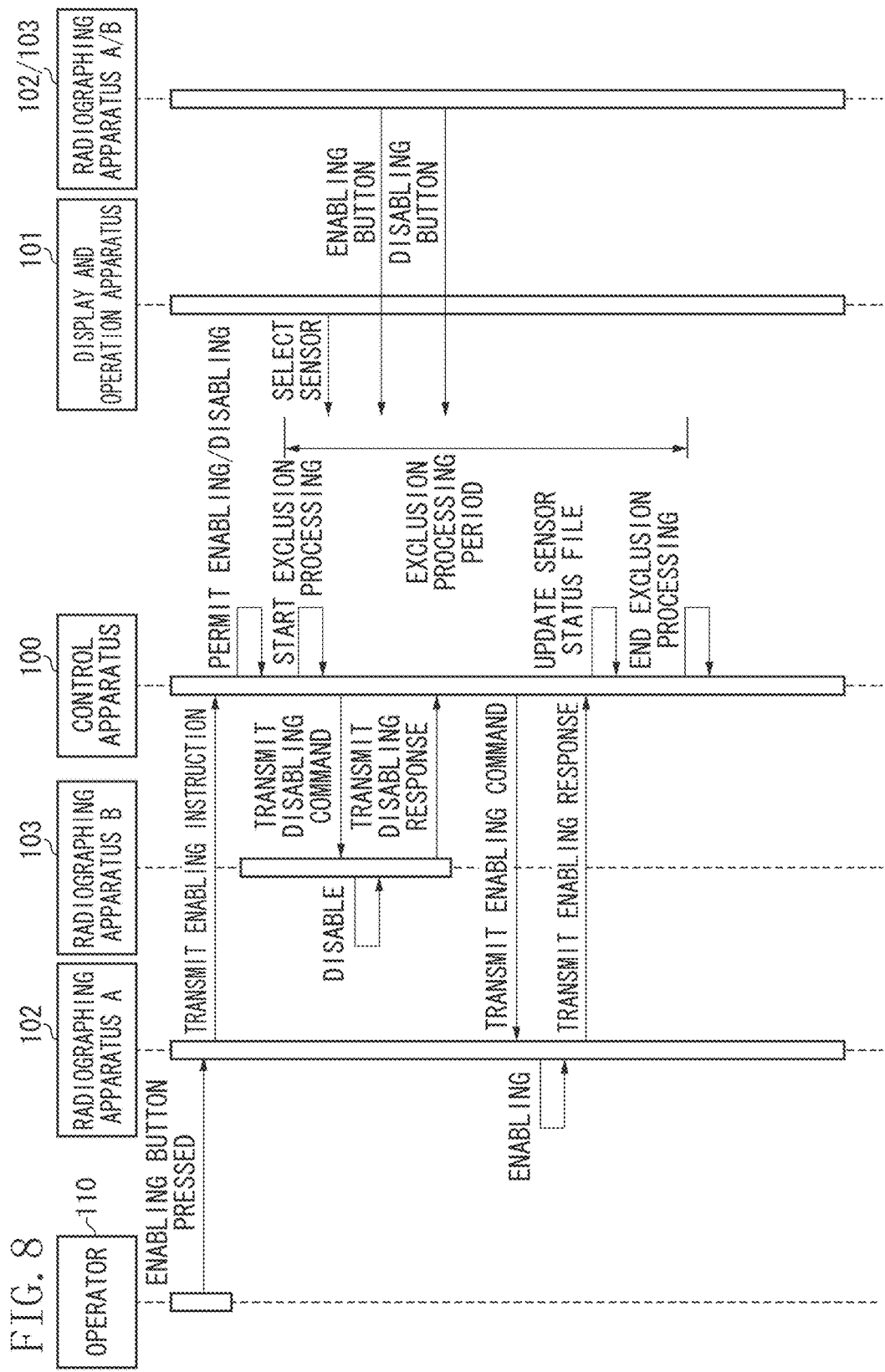
FIG. 8 is a sequence diagram illustrating operation procedures according to the first example embodiment of the present invention.
Figure 9:
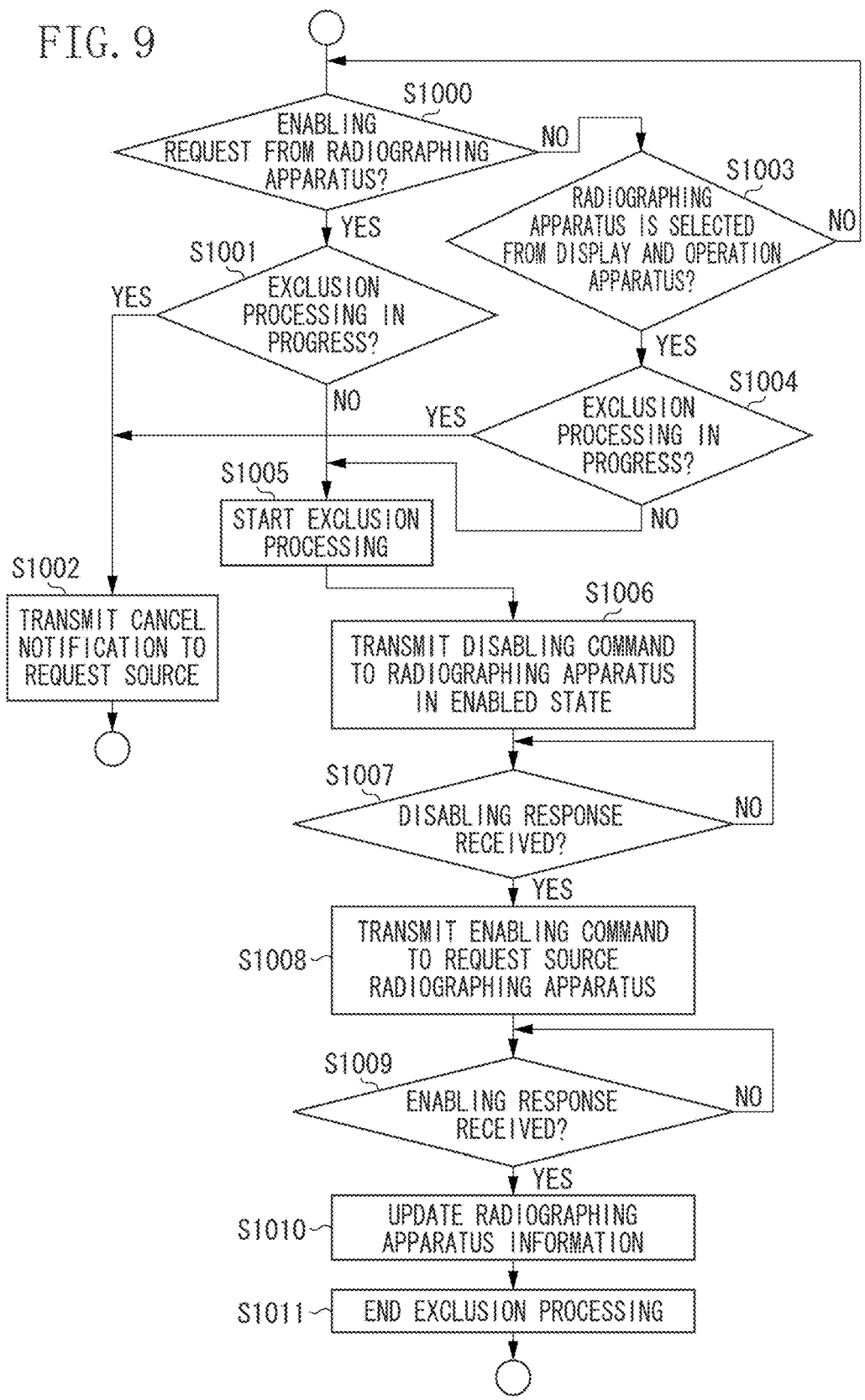
FIG. 9 is a flowchart illustrating an operation procedure according to the first example embodiment of the present invention.

FIG. 8 is a sequence diagram illustrating processing of the radiographing system according to the first example embodiment of the present invention. FIG. 9 is a flowchart illustrating processing of the radiographing system according to the first example embodiment of the present invention.

As illustrated in FIG. 8, when the operator presses the enabling instruct unit 107 of the enabling target radiographing apparatus A, an enabling instruction is transmitted from the radiographing apparatus A to the control apparatus 100. When the control apparatus 100 receives the enabling instruction from the radiographing apparatus A (YES in step S1000), the processing proceeds to step S1001. In step S1001, the control apparatus 100 checks whether the radiographing system is currently performing the exclusion processing in which the radiographing system inhibits an interrupt from another radiographing apparatus B in the form of a status transition request.

When the radiographing system is currently performing the exclusion processing (YES in step S1001), the processing proceeds to step S1002. In step S1002, the control apparatus 100 notifies the request source of the cancellation and notifies the operator that the enabling instruction has not been accepted. More specifically, the control apparatus 100 transmits the cancel notification to the radiographing apparatus A of which the enabling instruct unit 107 has been pressed. More specifically, the radiographing apparatus A cannot be enabled.

On the other hand, when the radiographing system is not currently performing the exclusion processing (NO in step S1001), the processing proceeds to step S1005. In step S1005, the control apparatus 100 starts the exclusion processing. The control apparatus 100 receives neither an enabling instruction nor a disabling request from the radiographing apparatuses A and B until the exclusion processing is completed. More specifically, during a predetermined period of time after receiving the enabling instruction from the enabling instruct unit 107, the control apparatus 100 is cancelling the enabling of another radiographing apparatus B. In other words, when a predetermined period of time has elapsed after receiving the enabling instruction from the enabling instruct unit 107, the control apparatus 100 permits the enabling of another radiographing apparatus B.

In step S1006, the control apparatus 100 transmits a disabling command to the radiographing apparatus B kept in the enabled state. The radiographing apparatus B is disabled so as to enter the disabled state, and transmits a disabling response to the control apparatus 100. When the control apparatus 100 receives the disabling response (YES in step S1007), the processing proceeds to step S1008. In step S1008, the control apparatus 100 transmits an enabling command to the request source, i.e. the radiographing apparatus A. The radiographing apparatus A performs the enabling, and when it enters the enabled state, the radiographing apparatus A transmits an enabling response to the control apparatus 100. The control apparatus 100 enables the radiographing apparatus A which has received the enabling instruction from the enabling instruct unit 107, to shift to a radiation detectable state. When the control apparatus 100 receives the enabling response (YES in step S1009), the processing proceeds to step S1010. In step S1010, the control apparatus 100 updates the information in the radiographing apparatus information storage unit 522. In step S1011, the control apparatus 100 ends the exclusion processing.

More specifically, when the operator selects another radiographing apparatus B via the radiographing apparatus selection unit 540 immediately after issuing the enabling instruction to one radiographing apparatus A via the enabling instruct unit 107, the control apparatus 100 cancels the selection of another radiographing apparatus B. When the operator issues an enabling instruction to enable another radiographing apparatus B via the enabling instruct unit 107 of another radiographing apparatus B immediately after selecting one radiographing apparatus A via the radiographing apparatus selection unit 540, the control apparatus 100 cancels the enabling instruction.

In other words, after issuance of an enabling instruction via the enabling instruct unit 107 and before completion of the enabling of the radiographing apparatus A, the control apparatus 100 is cancelling the enabling of the other radiographing apparatus B. After completion of the enabling of the radiographing apparatus A which has received the enabling instruction via the enabling instruct unit 107, the control apparatus 100 permits the enabling of another radiographing apparatus B.

On the other hand, when the control apparatus 100 does not receive the enabling instruction from the radiographing apparatus A (NO in step S1000), the processing proceeds to step S1003. In step S1003, the control apparatus 100 checks whether a radiographing apparatus selection command has been transmitted from the display and operation apparatus 101. When the radiographing apparatus selection command has not been transmitted from the display and operation apparatus 101 (NO in step S1003), the processing returns to step S1000. On the other hand, when the radiographing apparatus selection command has been transmitted from the display and operation apparatus 101 (YES in step S1003), the processing proceeds to step S1004. In step S1004, the control apparatus 100 checks whether the exclusion processing is currently being performed. When the exclusion processing is currently being performed (YES in step S1004), the processing proceeds to step S1002. In step S1002, the control apparatus 100 transmits a cancel notification to the display and operation apparatus 101. On the other hand, when the exclusion processing is not currently being performed (NO in step S1004), the processing proceeds to step S1005. In step S1005, the radiographing apparatus is switched over.

The above-described procedures prevents the radiographing apparatuses A and B from entering the enabled state at the same time, and the radiographing apparatus switching can be performed from the radiographing apparatus sides. The above-described procedures indicate that processing can be suitably performed even when the operator presses the enabling instruct unit 107 of the radiographing apparatus A or B, and the radiographing apparatus selection button 221 or 222 of the display and operation apparatus 101 at the same time. Although, in the present example embodiment, switching is performed between two different radiographing apparatuses, the present invention is also applicable to three or more radiographing apparatuses.

According to the present example embodiment, a radiographing system including a plurality of radiographing apparatuses 102 and 103 for detecting a radiation and the control apparatus 100 for controlling a plurality of the radiographing apparatuses 102 and 103 includes the enabling instruct unit 107 for issuing an enabling instruction for enabling one radiographing apparatus from the radiographing apparatuses 102 and 103. When an enabling instruction for enabling one radiographing apparatus 102 is issued from the enabling instruct unit 107, the control apparatus 100 restricts the enabling of another radiographing apparatus 103 during a predetermined period of time after receiving the enabling instruction. When the enabling instruct unit 107 enables one radiographing apparatus 102, the control apparatus 100 disables another radiographing apparatus 103. More specifically, when the radiographing apparatus 102 which has received the enabling instruction via the enabling instruct unit 107 is enabled, the control apparatus 100 disables another radiographing apparatus 103 and then enables the radiographing apparatus 102 which has received the enabling instruction.

This configuration makes it possible to suitably control the enabling and disabling of a plurality of radiographing apparatuses.

Figure 10:
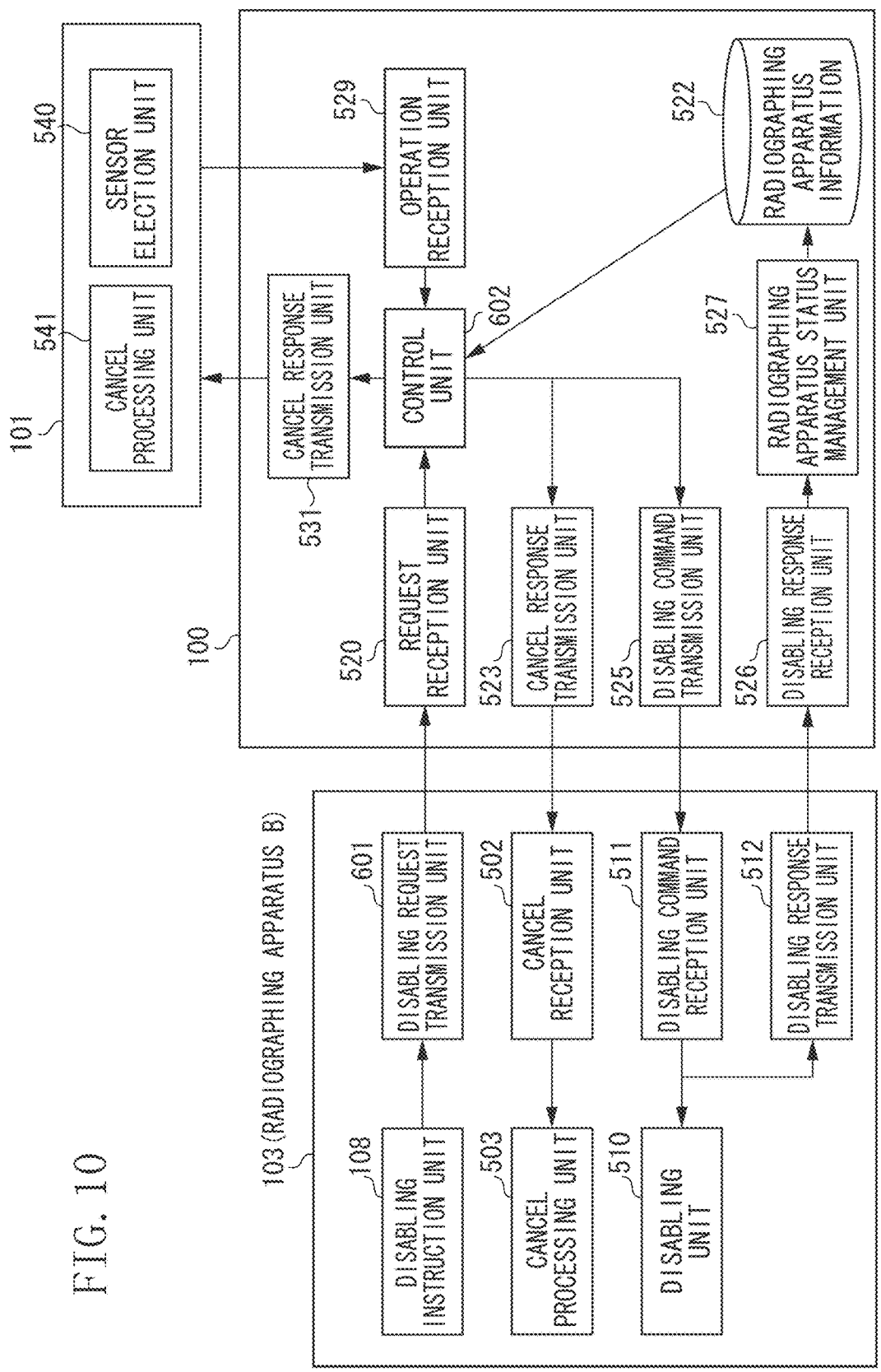
FIG. 10 is a block diagram illustrating a configuration according to a second example embodiment of the present invention.
Figure 11:
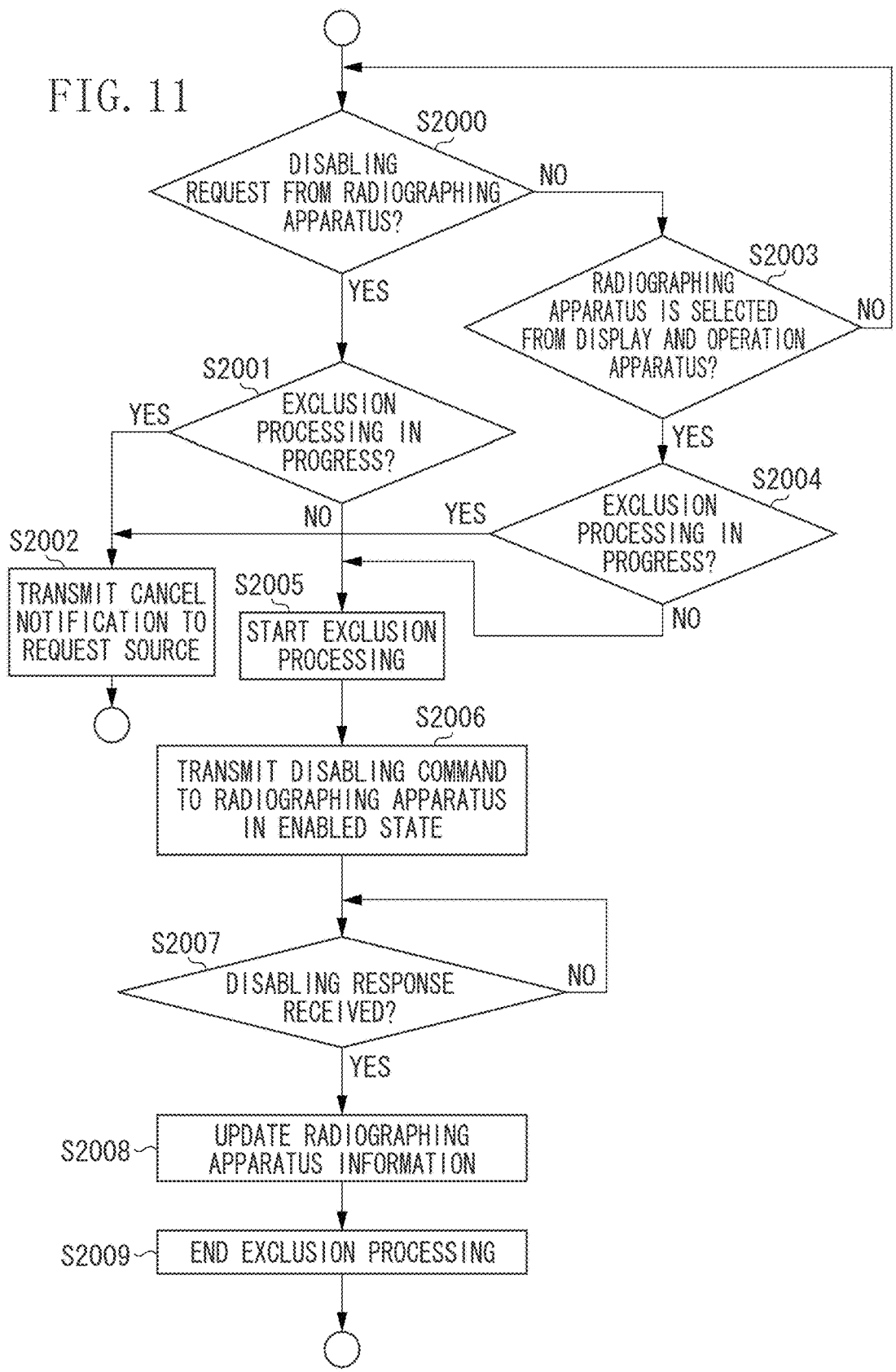
FIG. 11 is a flowchart illustrating an operation procedure according to the second example embodiment of the present invention.

A second example embodiment of the present invention will be described below with reference to FIGS. 10 and 11.

For components identical to those illustrated in FIG. 5, redundant descriptions will be omitted.

The imaging of fingers is performed according to the first example embodiment, and the operator confirms a taken image on the display and operation apparatus 101. If there is no problem, all of imaging protocols for the subject are completed. Then, the operator presses an End Inspection 211 in the imaging screen to end the inspection. Upon completion of the inspection, taken images and imaging conditions are transmitted to a Picture Archiving and Communication System (PACS) and a radiology information system (RIS) via the in-hospital network 104 for the purpose of diagnosis and accounting processing.

Particularly with respect to radiographing apparatuses of automatic detection type, it is important to disable the radiographing apparatus to prevent transmission of incorrect radiation image data in a case where inspections are not to be performed for a certain period of time or in a case where a specific radiographing apparatus is not to be used.

A configuration for disabling the radiographing apparatus B will be described below. The operator presses the disabling instruct unit 108 provided as a button on the radiographing apparatus B to disable the radiographing apparatus B. Instead of a button, the disabling instruct unit 108 illustrated in FIG. 10 may be a switch or speech input device as long as a disabling request can be made.

When input is done from the disabling instruct unit 108, a disabling request is transmitted from a disabling request transmission unit 601 to the control apparatus 100. The transmitted disabling request is received by the instruction reception unit 520. The control unit 602 determines whether the disabling of the radiographing apparatus B is possible. The control unit 602 checks whether another radiographing apparatus is currently performing status transition. When another radiographing apparatus is not currently performing status transition, the control unit 602 permits the disabling of the radiographing apparatus B. The status transition being in progress refers to a state where the exclusion processing for the radiographing apparatus A or B is currently being performed.

When the control unit 602 does not permit the disabling of the radiographing apparatus B, a cancel response is transmitted from the cancel response transmission unit 523 to the radiographing apparatus B. The transmitted cancel response is received by the cancel reception unit 502. The cancel processing unit 503 performs cancel processing. The cancel processing unit 503 generates an electronic sound such as a pip sound to feed back to the operator the information indicating that the pressing of the disabling button has not worked.

When the control unit 602 permits the disabling of the radiographing apparatus B, the control unit 602 performs the exclusion processing via an exclusive control unit 530 to inhibit an interrupt of a status transition request, by using, for example, a semaphore or mutex on a program. Then, a disabling command is transmitted from the disabling command transmission unit 525. The transmitted disabling command is received by the disabling command reception unit 511 of the radiographing apparatus B and then is transmitted to the disabling unit 510. The radiographing apparatus B enters the disabled state and the status display unit 106 turns OFF.

Upon completion of the disabling of the radiographing apparatus B, a disabling response received from the disabling unit 510 is transmitted from the disabling response transmission unit 512 to the control apparatus 100. In the control apparatus 100, the transmitted disabling response is received by the enabling/disabling response reception unit 526, and the radiographing apparatus status management unit 527 updates the information in the radiographing apparatus information storage unit 522.

In the above-described configuration, the radiographing apparatus A can be disabled by pressing the disabling instruct unit 108 provided as a button on the radiographing apparatus B.

A flow of processing according to the second example embodiment will be described below with reference to FIG. 11. When the operator presses the disabling button of the radiographing apparatus B to be disabled, a disabling request is transmitted from the radiographing apparatus B 103 to the control apparatus 100. When the control apparatus 100 receives the disabling request from the radiographing apparatus B (YES in step S2000), the processing proceeds to step S2001. In step S2001, the control apparatus 100 checks whether the exclusion processing is currently being performed. When the exclusion processing is currently being performed (YES in step S2001), the processing proceeds to step S2002. In step S2002, the control apparatus 100 transmits a cancel notification to the request source to notify the operator that the disabling request has not been accepted.

On the other hand, when the exclusion processing is not currently being performed (NO in step S2001), the processing proceeds to step S2005. In step S2005, the control apparatus 100 performs the exclusion processing. After that, the control apparatus 100 receives neither an enabling instruction nor a disabling request until the exclusion processing is completed. In step S2006, the control apparatus 100 transmits a disabling command to the radiographing apparatus B kept in the enabled state. The radiographing apparatus B disables the radiographing apparatus to enter the disabled state. When the radiographing apparatus is disabled, the radiographing apparatus B transmits a disabling response to the control apparatus 100. When the control apparatus 100 receives the disabling response (YES in step S2007), the processing proceeds to step S2008. In step S2008, the control apparatus 100 updates the radiographing apparatus information 230. In step S2009, the control apparatus 100 ends the exclusion processing. Steps S2003, S2004, and S2008 are similar to steps S1003, S1004, and S1010 illustrated in FIG. 9.

The above-described procedures enable suitably shifting the radiographing apparatus B from the enabled state to the disabled state.

Figure 12:
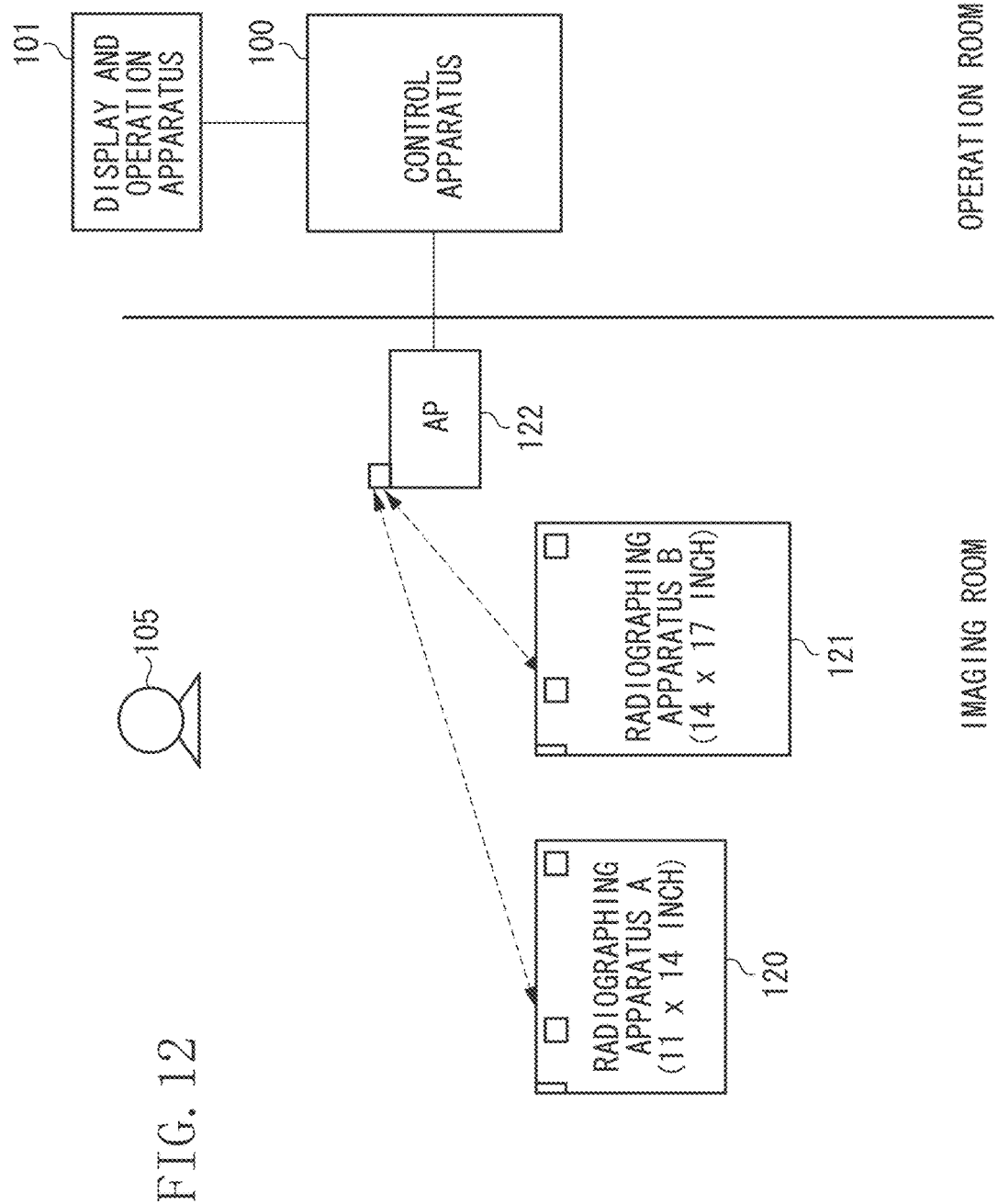
FIG. 12 is a block diagram illustrating a configuration according to a third example embodiment of the present invention.

FIG. 12 is a block diagram illustrating a configuration according to a third example embodiment of the present invention. In the first and the second example embodiments, the radiographing apparatuses A and B and the control apparatus 100 are connected via Ethernet (registered trademark) cables. Commands such as an enabling request, a disabling request, an enabling command, a disabling command, an enabling response, and a disabling response, and image data are transmitted and received via the cables.

Referring to FIG. 12, in the third example embodiment, the radiographing apparatuses A and B and the control apparatus 100 are connected via wireless communication instead of physical cables. The wireless radiographing apparatuses A and B communicate with the control apparatus 100 via an access point AP 122. The AP 122 and the control apparatus 100 are connected via an Ethernet cable. While the radiographing apparatuses and the AP 122 are connected via wireless communication, the configurations, flowcharts, and sequences for achieving the third example embodiment of the present invention remain unchanged.

Figure 13:
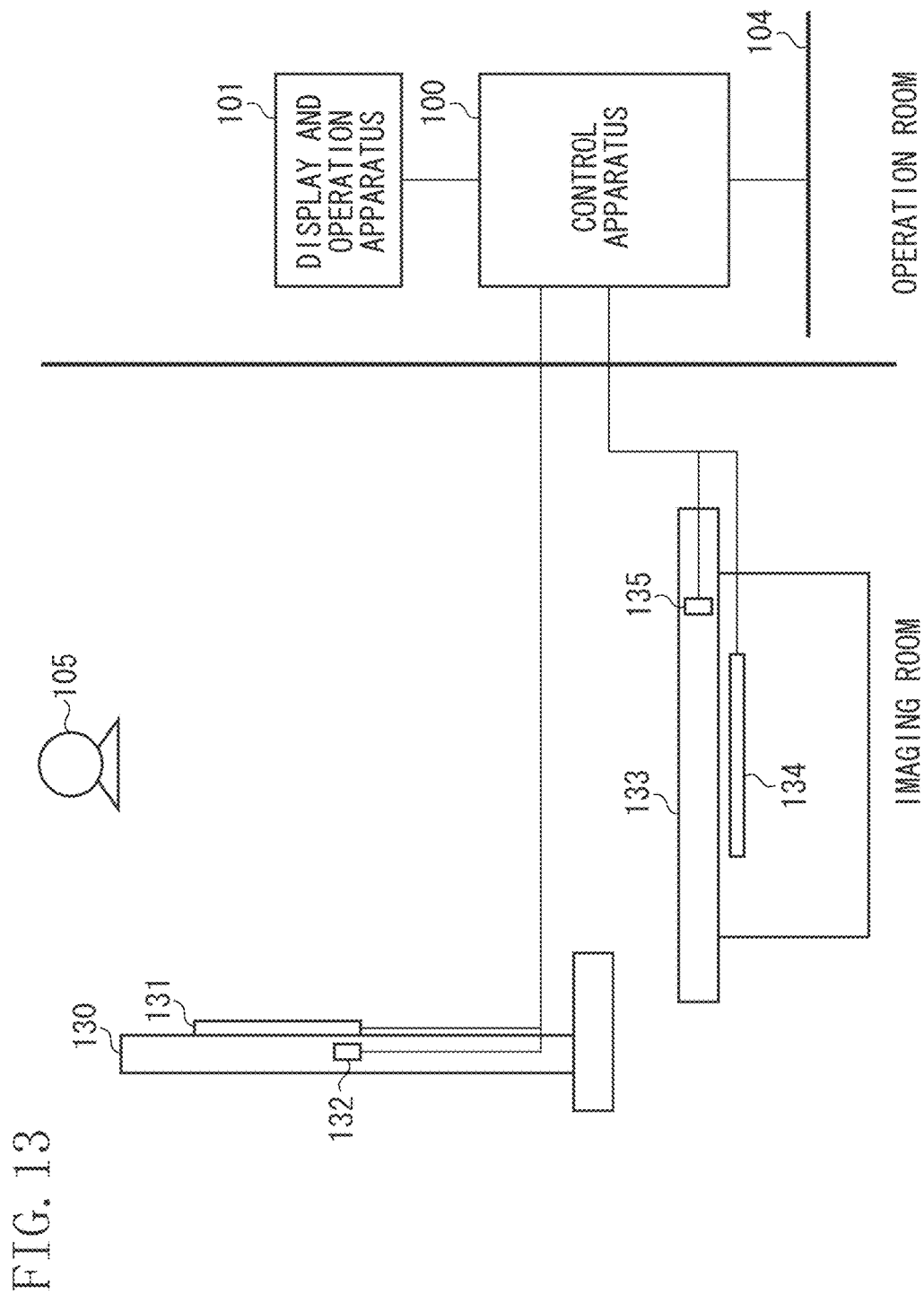
FIG. 13 is a block diagram illustrating a configuration according to a fourth example embodiment of the present invention.

FIG. 13 is a block diagram illustrating a configuration of a fourth example embodiment of the present invention. In the first and the second example embodiments, the enabling instruct unit 107 and the disabling instruct unit 108 are provided as buttons on the radiographing apparatuses A and B which are cassette type radiographing apparatuses. When a cassette is attached to a rack, it may become difficult to press a button depending on the attachment position. Accordingly, in the present example embodiment, the enabling instruct unit 107 and the disabling instruct unit 108 are provided as buttons on racks to which the radiographing apparatuses A and B are attached.

An enabling instruct unit button 132 is attached to a stand 130 which is an upright type rack, and an enabling instruct unit button 135 is attached to a bed 133 which is a lying type rack. Button functions of the enabling instruct unit 107 and the disabling instruct unit 108 are similar to those in the first and the second example embodiments.

Other Embodiments

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to example embodiments, it is to be understood that the invention is not limited to the disclosed example embodiments. The scope of the following claims is to be accorded the broadest interpretation so as to encompass all such modifications and equivalent structures and functions.

This application claims the benefit of Japanese Patent Application No. 2016-087441, filed Apr. 25, 2016, which is hereby incorporated by reference herein in its entirety.

What is claimed is:

1. A radiographing system comprising:
a plurality of radiographing apparatuses for detecting a radiation,
a control apparatus for controlling the plurality of the radiographing apparatuses, and
wherein the radiographing system comprises an enabling instruct unit to issue an instruction for enabling one of the radiographing apparatuses,
wherein, when the instruction for enabling the one of the radiographing apparatuses is issued from the enabling instruct unit, the control apparatus restricts an enabling of another of the radiographing apparatuses during a predetermined period of time after receiving the enabling instruction.

2. The radiographing system according to claim 1, wherein, in the predetermined period, the control apparatus cancels the enabling of the another of the radiographing apparatuses.

3. The radiographing system according to claim 1, wherein, after the predetermined period has elapsed, the control apparatus permits the enabling of the another of the radiographing apparatuses.

4. The radiographing system according to claim 1, wherein, after performing processing for disabling the another of the radiographing apparatuses, the control apparatus enables the one of the radiographing apparatuses which has received the enabling instruction via the enabling instruct unit.

5. The radiographing system according to claim 1, wherein the control apparatus enables the one of the radiographing apparatuses which has received the enabling instruction via the enabling instruct unit to enter a radiation detectable state.

6. The radiographing system according to claim 1, further comprising a selection unit connected to the control apparatus and configured to select one of the radiographing apparatuses for detecting a radiation.

7. The radiographing system according to claim 6, wherein, when the instruction for enabling the another of the radiographing apparatuses is issued via the enabling instruct unit of the another of the radiographing apparatuses immediately after selecting the one of the radiographing apparatuses via the selection unit, the control apparatus cancels the enabling instruction.

8. The radiographing system according to claim 6, wherein, when the another of the radiographing apparatuses is selected by the selection unit immediately after issuing the instruction for enabling the one of the radiographing apparatuses via the enabling instruct unit, the control apparatus cancels the selection of the another of the radiographing apparatuses.

9. The radiographing system according to claim 1, wherein, before completion of the enabling of the one of the radiographing apparatuses which has received the enabling instruction via the enabling instruct unit, the control apparatus is cancelling the enabling of the another of the radiographing apparatuses.

10. A radiographing system according to claim 1, wherein, after completion of the enabling of the one of the radiographing apparatuses which has received the enabling instruction via the enabling instruct unit, the control apparatus permits the enabling of the another of the radiographing apparatuses.

11. A radiographing system comprising:
a plurality of radiographing apparatuses for detecting a radiation,
a control apparatus for controlling the plurality of the radiographing apparatuses, and
an enabling instruct unit for issuing an instruction for enabling one of the radiographing apparatuses,
wherein, when enabling the one of the radiographing apparatuses which has received the enabling instruction via the enabling instruct unit, the control apparatus enables the one of the radiographing apparatuses which has received the enabling instruction after disabling another of the radiographing apparatuses.

12. A radiographing system comprising:
a plurality of radiographing apparatuses for detecting a radiation, and
a control apparatus for controlling the plurality of the radiographing apparatuses, wherein, when an instruction for enabling one of the radiographing apparatuses is issued, the control apparatus restricts the enabling of another of the radiographing apparatuses during a predetermined period of time after receiving the enabling instruction.

13. A method of controlling a plurality of radiographing apparatuses for detecting a radiation, the method comprising:

issuing an instruction for enabling one of the radiographing apparatuses; and restricting, when the one of the radiographing apparatuses is enabled based on the enabling instruction, an enabling of another of the radiographing apparatuses during a predetermined period of time after receiving the enabling instruction.

14. A method of controlling a plurality of radiographing apparatuses for detecting a radiation, the method comprising:

issuing an instruction for enabling one of the radiographing apparatuses;

disabling another of the radiographing apparatuses when enabling the one of the radiographing apparatus which has received the enabling instruction; and enabling the one of the radiographing apparatuses which has received the enabling instruction after disabling another of the radiographing apparatuses.

15. A method of controlling a plurality of radiographing apparatuses for detecting a radiation, the method comprising:

issuing an instruction for enabling one of the radiographing apparatuses; and restricting an enabling of another of the radiographing apparatuses during a predetermined period of time after receiving the enabling instruction.

* * * * *